United States Patent [19]

Pieniak

[11] Patent Number: 4,560,372
[45] Date of Patent: Dec. 24, 1985

[54] STABLE DISPOSABLE ABSORBENT STRUCTURE

[75] Inventor: Heinz A. Pieniak, North Brunswick, N.J.

[73] Assignee: Personal Products Company, Milltown, N.J.

[21] Appl. No.: 606,075

[22] Filed: May 1, 1984

[51] Int. Cl.$^4$ ............................................. A41B 13/02
[52] U.S. Cl. ..................... 604/369; 604/368; 604/370; 604/374; 604/366
[58] Field of Search ............... 604/369, 368, 370, 374, 604/372, 378, 379, 366, 375

[56] References Cited

U.S. PATENT DOCUMENTS

| | | | |
|---|---|---|---|
| 4,235,237 | 11/1980 | Mesek et al. | 604/369 |
| 4,323,069 | 4/1982 | Ahr et al. | 604/372 |
| 4,381,783 | 5/1983 | Elias | 604/378 |
| 4,500,315 | 2/1985 | Pieniak et al. | 604/379 |

Primary Examiner—C. Fred Rosenbaum
Assistant Examiner—Christa K. Scott
Attorney, Agent, or Firm—Martha A. Michaels

[57] ABSTRACT

A disposable absorbent product is provided in the form of a layered structure. A first fibrous layer of resilient fibers contains superabsorbent and is superposed on a layer of hydrophilic material. The layers are unpressed and slit followed by extrusion to open the slits to provide apertures. The structure is used as the absorbent core in diapers, sanitary napkins, wound dressings and the like.

11 Claims, 4 Drawing Figures

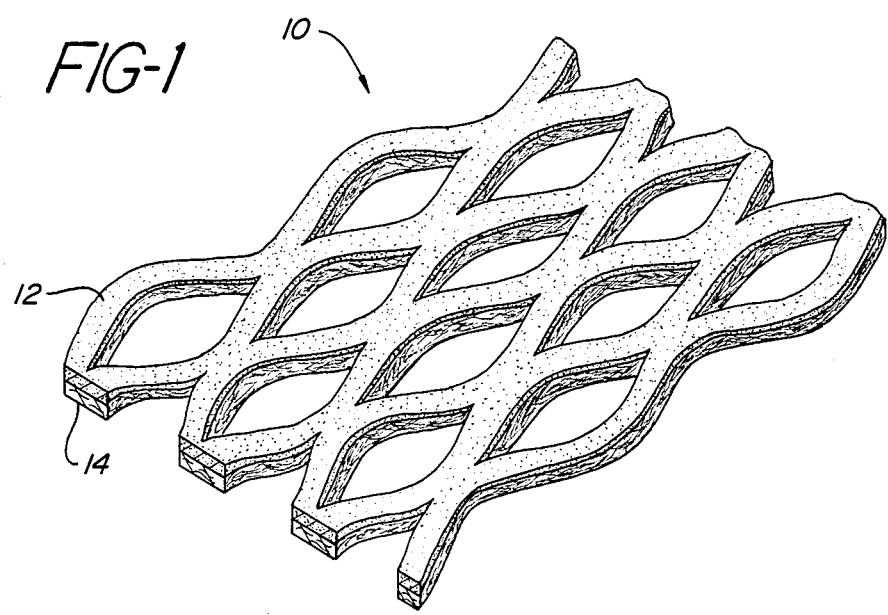
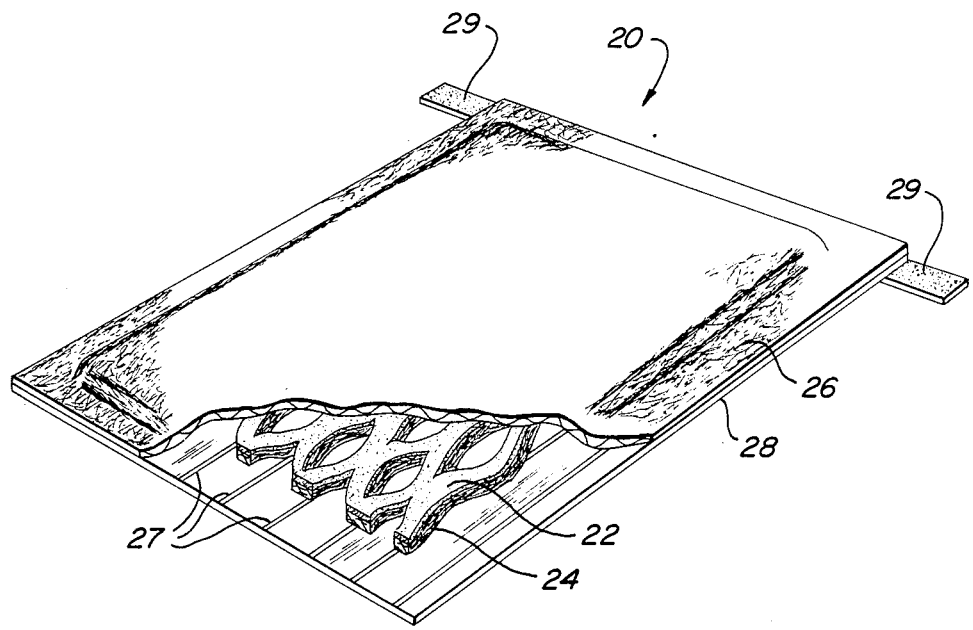

STABLE DISPOSABLE ABSORBENT STRUCTURE

BACKGROUND OF THE INVENTION

The present invention relates to new and improved stable disposable absorbent structures and more particularly, to diapers, sanitary napkins, wound dressings and the like containing the new absorbent structures as the absorbent core of the product.

Disposable absorbent products have been known for some time including such products as disposable napkins, wound dressings, bandages, incontinent pads and the like. The products incorporate an absorbent batt which is used to absorb and hold or contain body fluids. Initially, in many of these products, especially diapers and sanitary napkins, the absorbent batt comprised what is termed "wadding" or plies of tissue. The wadding was disposed between a liquid-impermeable backing and a liquid-permeable facing and the plies of tissue were used to absorb and, hopefully, contain the liquid within the product. A diaper which utilizes such an absorbent core is disclosed in U.S. Pat. No. Re. 26,151.

The wadding type of product was replaced, for the most part, by an improved absorbent batt which comprises what is termed "fluffed woodpulp fibers". This absorbent batt comprises a layer of individualized woodpulp fibers with the layer having substantial thickness. A diaper which incorporates such a woodpulp absorbent batt is described in U.S. Pat. No. 2,788,003. This diaper had improved absorbent capacity and somewhat better containment than a diaper using a wadding layer. Also, the fluffed woodpulp layer is quite soft, flexible, and conformable and hence, produces an improved diaper over diapers using wadding as the absorbent layer.

Though the fluffed woodpulp absorbent batts have improved capacity, the efficiency with which the capacity is used in a diaper or sanitary napkin is poor. One of the reasons for this is that the fluffed woodpulp absorbent batt tends to break apart upon flexing. Furthermore, once the absorbent batt has accepted a substantial amount of liquid the cellulosic fibers tend to collapse, sometimes causing liquid to be squeezed from the product and to leak. Another reason is that the fluid to be absorbed is generally deposited in a localized area and the ability of the fluid to move along the plain of the batt is poor. The fluid tends to follow a radial wicking path and consequently moves to the closest edge of the batt where it generally is no longer contained and the product leaks. The only way in which the capacity can be increased is to add more pulp thus compounding the problems already present and thickening the product making it more bulky.

In answer to some of the problems U.S. Pat. No. 3,017,304 incorporated in the absorbent batt a densified paper-like layer. This paper-like layer acts as a wick, i.e., liquid which is placed on the layer tends to move rapidly along the plane of the layer. When incorporated in combination with fluffed woodpulp fiber the liquid wicks along the paper-like densified layer and tends to use the absorbent capacity of the absorbent batt much more efficiently. However, the paper-like densified layer is subject to fracture and though it stabilizes the absorbent batt, to some degree, separation still occurs. Diapers which incorporated this paper-like layer combined with fluffed woodpulp are disclosed and described in U.S. Pat. Nos. 3,612,055 and 3,938,522. This concept of combining wicking ability or a capillary skin layer with fluffed woodpulp fibers has gained wide acceptance in many absorbent products, including disposable diapers and sanitary napkins. These products still do not totally contain the absorbed liquid. It is probable that these products will leak before the full capacity of the batt is used or before the entire liquid void by the user is absorbed. This is especially true when pressure is placed on the batt while wet. For example, a baby sitting down on a previously wetted diaper will very often cause the batt to leak. Furthermore, when providing a paper-like densified layer, the absorbent batt becomes more rigid and less conformable thus causing gaps at the side which permit leakage.

A number of years ago, in answer to increasing capacity of absorbent products, "superabsorbent materials" (i.e., materials which will absorb many times their weight in liquid) were developed. Since the development of such materials, attempts to incorporate them in absorbent products, such as diapers, to enhance the absorption performance of these products have been made. Theoretically, a minimum amount of superabsorbent incorporated in a product would make that product perform as well or better than the prior art products. Perhaps one of the first products to incorporate such a superabsorbent material in a disposable diaper is disclosed in U.S. Pat. No. 3,670,731. This patent discloses an absorbent dressing comprising an absorbent layer sandwiched between a permeable facing and an impermeable backing sheet. The absorbent layer contains water-insoluble cross-linked hydrocolloidal polymer as the superabsorbent material.

Even though superabsorbent materials have been available for some time, they have not gained wide acceptance in absorbent products such as disposable diapers, sanitary napkins, wound dressings, incontinent pads and the like. A primary reason for this lack of acceptance of superabsorbents is failure to develop a product capable of economically utilizing a highly increased absorptive capacity of the superabsorbent material. In order to economically utilize a superabsorbent, the liquid being absorbed must be readily accepted and placed in contact with the superabsorbent material. Furthermore, as the superabsorbent material absorbs liquid it must be allowed to swell. If the superabsorbent is prevented from swelling it will cease absorbing liquid. Hence, if the superabsorbent material is to function in absorbent products, such as disposable diapers, sanitary napkins and the like, wherein the liquid to be absorbed is placed in a small void area, the structure of the absorbent layer containing superabsorbent materials must have certain characteristics. Over the years a number of techniques have been disclosed in an attempt to provide structures which make efficient use of the superabsorbent material. Such products are disclosed in U.S. Pat. Nos. 4,103,062, 4,102,340 and 4,235,237. In addition, methods for incorporating superabsorbents into suitable layers or suitable configurations which can be placed in an absorbent product are disclosed in U.S. Pat. Nos. 4,186,165, 4,340,057 and 4,364,992. To date, none of these products has met with any substantial commercial success.

The present invention provides a new and improved absorbent product which is dimensionally stable when in use and which possess a conformable absorbent core containing superabsorbent material. The new absorbent product will contain absorbed liquid even when pressure is placed upon the product during use.

SUMMARY OF THE INVENTION

The present invention provides an absorbent product which comprises a layered structure. The layered structure is comprised of a first fibrous layer substantially of resilient fibers and containing at least about 10% by weight of superabsorbent material. A second layer of hydrophilic porous material is substantially coextensive with the first layer and is superposed on the first layer. The two layers are subjected to at least about 200 psi pressure in the presence of from about 10% to about 50% moisture. The structure is provided with longitudinal parallel slits in staggered rows. The slits being at least about 0.5 inch in length and the rows being from about 0.1 to about 0.5 inches apart. The slit structure is extended, transversely, to provide an apertured structure and the apertured structure is sandwiched between a liquid-impermeable barrier and a liquid-permeable facing. The absorbent product is provided with a multiplicity of what might be called reservoirs which are the apertures in the layered structure. These apertures readily accept liquid and the layered structure absorbs the liquid utilizing the superabsorbent. The second layer of hydrophilic porous material, after having been subjected to pressure, provides a wicking layer which assists in wicking the liquid to other portions of the layered structure. The absorbent product is light-weight, stable, readily accepts, transports and retains liquid. The product will retain at least 150 milliters of body exudate such as urine. The apertured layered structure sandwiched between the backing and the facing conforms easily to the body shape of the wearer.

For instance, the layered structure provides a highly desirable wound dressing. Particularly for regions such as knees or elbows, wherein conformity to the body shape is highly desirable.

The absorbent product of the present invention is suitable for use in a disposable diaper, a sanitary napkin, an incontinent pad, a wound dressing, bandages and the like.

BRIEF DESCRIPTION OF THE DRAWINGS

FIG. 1 is a perspective view of one embodiment of the present invention;

FIG. 2 is a perspective view of a diaper product incorporating another embodiment of the present invention;

DETAILED DESCRIPTION OF THE INVENTION

Figure 3:
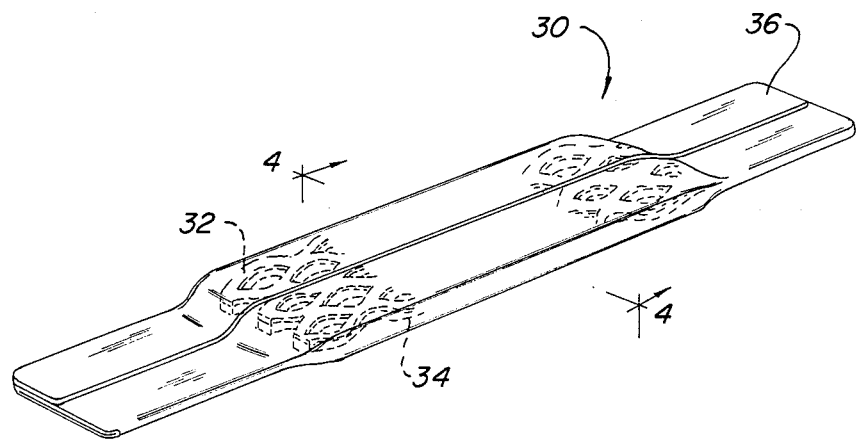
FIG. 3 is a perspective view of a sanitary napkin utilizing a still further embodiment of the present invention.

FIG. 1 depicts a perspective view of a layered structure 10 wherein a first fibrous layer 12, of substantially resilient fibers and containing at least about 10% superabsorbent, is superposed on a cellulosic fibrous layer 14. The cellulosic fibers are placed on the first fibrous layer before the slits and transverse extension are carried out. The parallel staggered rows of slits and the transverse extension of the layered structure provide apertures 16. When the layered structure 10 is used in a product to absorb body exudate, the apertures 16 act as reception wells and rapidly receive large quantities of exudate. The layered structure 10 readily absorbs the exudate and the cellulosic fibrous layer 14 wicks liquid along the layered structure thus exposing the liquid to the superabsorbent contained in the first fibrous layer 12.

FIG. 2 depicts a disposable diaper 20. The diaper comprises a liquid-permeable facing 42. The layered structure 44 is contained between the liquid-permeable facing 42 and the liquid-impermeable backing 46. The layered structure is held in place between the facing and the backing by glue lines 47. The first fibrous layer of the layered structure 44 is in contact with the facing sheet 42. Tape tabs 48 are placed at one end of the diaper on each side to provide a securement means for securing the diaper about the waist of the wearer when the diaper is being worn. When urine is excreted by the wearer, it penetrates the facing sheet 42 and lodges in the apertures 49 provided by the layered structure 44. The diaper readily receives and retains at least 150 milliliters of urine.

Figure 4:
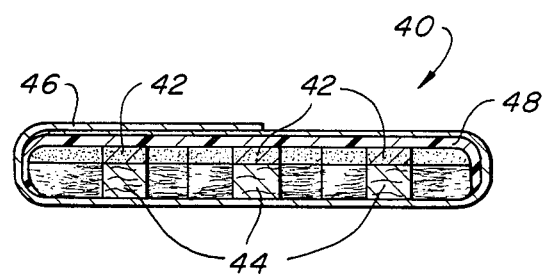
FIG. 4 is a cross-sectional view taken along lines 4—4 of FIG. 3.

FIG. 3 illustrates a sanitary napkin 30 containing a layered structure 32. The layered structure is placed in the napkin, as depicted, with the first fibrous layer appearing on the underside. This is because the napkin, as it is depicted in FIG. 3, has the bottom side facing upward. FIG. 4 is a cross-sectional view of the napkin in FIG. 3 along lines 4—4. The layered structure 42 contains a first fibrous layer 44 having superabsorbent therein and a second layer 46 of hydrophilic porous material, in this case acrylic fibers, which assist in wicking the body exudate to other portions of the layered structure. The sanitary napkin 40 has a liquid-impermeable sheet 45 encompassing the bottom and each side of the product. The product then is covered by a liquid-permeable over-wrap 46 to provide a soft, comfortable product. As can be seen, by viewing FIGS. 3 and 4, the sanitary napkin is very thin.

These and other products, such as incontinent pads, wound dressings and the like, may be made from the absorbent layered product depicted in FIG. 1.

The preferred layered structure has a first fibrous layer of resilient fibers. These fibers are both wet and dry resilient and generally are synthetic staple fibers, such as polyester, polyethylene, polypropylene and the like. Generally, the fibers are air laid and lightly heat bonded. If the fibers selected are not thermoplastic, then a minor amount of thermoplastic fibers can be added to provide a binder fiber so that heat bonding can take place. After the air laid web is lightly bonded the web is placed in contact with superabsorbent material. The superabsorbent may be in a powder form in which case it can be distributed on one side of the formed web. If it is in granular form, the superabsorbent generally is slightly moistened and distributed substantially evenly on one side of the web. Another means of associating superabsorbent with the web is substantially saturating the web with a liquid monomer and then subjecting the web and the monomer to irradiation to polymerize and cross-link the monomer to form a water insoluble water swellable superabsorbent material. After placement of the superabsorbent material with the web, a layer of hydrophilic porous material, for example, woodpulp fiber, is superposed on the side of the web containing the largest portion of superabsorbent material. The two layers are subjected to compression in the presence of at least about 10% moisture, such that the superabsorbent material tends to be tacky and after compression the layered structure is of reduced thickness. Materials other than moisture may be used to render the superabsorbent tacky so long as the material does not interfere with the absorption properties. Suitable materials include polyethylene oxide, polyvinyl acetate, starches and other materials. The pressure used in the compression should be from about 200 psi to about 500 psi or more. The at least slightly compressed layered structure is then slit with staggered parallel rows of slits extending longitudinally on the web. Subsequent to slitting, the layered structure is extended transversely causing the slits to open and thus form apertures. The layered structure is now ready for use in an absorbent product. When the layered structure is utilized in a layered diaper, it is preferably secured either to the facing or the backing, or the facing is secured to the backing through the apertures formed in the layered structure. Such securement prevents the layered structure from changing position between the facing and the backing.

The slits may be transverse to the length of the structure and the extension longitudinal to provide apertures. For example, if the structure is to be used in a disposable diaper product, transverse slits are placed in the central portion of the structure resulting in apertures in the crotch region where receiving wells are most needed. An added benefit of using transverse slits in the crotch region is the narrowing of the structure in the crotch region when it is extended to provide the apertures.

The first fibrous layer of substantially resilient fibers is formed from synthetic fibers such as polyethylene, polypropylene, polyester, nylon (polyamide fibers) bicomponent fibers, mixtures thereof and the like. Cellulosic fibers, such as rayon, may be used but, generally the cellulosic type fiber tends to collapse when wet and it is preferred to have a wet resilient fiber. Generally, the fibers are carded or air laid to form a web which is then stabilized as needed. Stabilization may be achieved by heat-through bonding, adhesive bonding, point embossing with heater adhesive, or both, and the like. Other suitable procedures for forming a web include wet laying, spun bonding, laying of melt blown fibers, and other known techniques. The fibrous web preferably has a dry bulk of at least about 10 cc's per gram and a weight less than about 4 oz. per sq. yd. (about 150 grm per sq. meter).

The superabsorbent material present either on the fibers of the web or otherwise associated with the web is generally a water-swellable, water-insoluble polymeric substance capable of absorbing water in an amount which is at least 10 times the weight of the substance in its dry form.

The superabsorbent is in the form of fibers, spheres, particles, bits of film, globules, webs, film, foam or the like, or may be applied in the form of a liquid monomer solution which is subsequently polymerized. The superabsorbent prepared by polymerization of a monomer solution placed on fibers in a web is most frequently in the form of globules and bits of film-like particles in the web structure.

One type of superabsorbent material provides particles or fibers which may be described chemically as having a backbone of natural or synthetic polymers with hydrophilic groups or polymers containing hydrophilic groups being chemically bonded to the backbone or an intimate mixture therewith. Included in this class of materials are such modified natural and regenerated polymers as polysaccharides, including for example, cellulose and starch and regenerated cellulose which are modified by being carboxyalkylated, phosphonoalkylated, sulfoalkylated, or phosphorylated to render them highly hydrophilic. Such modified polymers may also be cross-linked to improve their water-insolubility.

These same polysaccharides may also serve, for example, as the backbone on to which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain of the general formula:

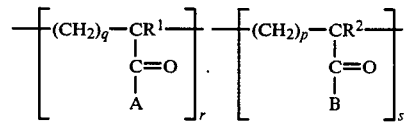

wherein A and B are selected from the group consisting of —$OR^3$, —O(alkali metal), —$OHNH_3$, —$NH_2$, wherein $R^1$, $R^2$, and $R^3$ are selected from the group consisting of hydrogen and alkylene having 1 to 4 or more carbon atoms wherein r is an integer having a value of 0 to about 5000 or more, s is an integer having a value of 0 to about 5000 or more, r plus s is at least 500, p is an integer having a value of 0 or 1, and q is an integer having a value of 1 to 4. The preferred hydrophilic chains are hydrolyzed polyacrylonitrile chains and copolymers of polyacrylamide and polysodium acrylate.

In addition to the modified natural and regenerated polymers, the hydrocolloid component may comprise wholly synthetic hydrophilic particles. Examples of those now known in the art are polyacrylonitrile fibers which may be modified by grafting moieties thereon such as polyvinylalcohol chains, polyvinyl alcohol itself, hydrophilic polyurethane, poly(alkyl phosphonates), partially hydrolyzed polyacrylamides (e.g., poly(N-N-dimethylacrylamide), sulfonated polystyrene, or a class of poly(alkyleneoxide). These highly hydrophilic synthetic polymers may be modified by other chemical treatments such as cross-linking or hydrolysis. Further examples known in the art are the non-ionic polymers such as polyoxyethylene, polyoxypropylene, and mixtures thereof which have been suitably cross-linked, either chemically or by irradiation. Still another more recent type is a derivative of isobutylenemalic and acrylate monomers, such as sodium, potassium, ammonium, (or a combination of cations), acrylate, may be placed on the absorbing layer by spraying or otherwise placing a solution thereon, followed by polymerization and cross-linking, for example, by irradiation.

In addition, naturally occurring materials such as gums may be used. Examples of such suitable gums include guar gums, acacia gums, locust bean gums and the like.

The superabsorbent is combined with the layered structure in such a manner as to remain substantially in the same position or region even though the layered structure may be moved about during manufacturing, packaging, or use. The superabsorbent is present in an amount of at least about 10% by weight of the first fibrous layer, and preferably from about 20% to about 90%. Any superabsorbent which absorbs large amounts of liquids is suitable for use in the layered structure of the present invention. It has been stated that it is preferred that the first fibrous layer be a fibrous web with a dry bulk of at least about 10 cc's per gram. The dry bulk is the area times thickness of the web under a load of 0.01 psi calculated in cubic centimeters. This value is divided by the weight in grams in order to provide the measurement in cubic centimeters per gram.

A layer of hydrophilic porous material is superposed on the first fibrous layer. Effective materials for forming this hydrophilic porous layer include tissue, lightly compressed woodpulp fibers, peat moss, acrylic fibers and the like. All of these materials provide a wicking layer which has a higher capillary pressure for any absorbed liquid than the first fibrous layer and hence, tends to transport the liquid to other regions of the product. The absorbent product of the present invention is a stable product which, upon manufacture and subsequent placement in a diaper product or a sanitary napkin product, remains stable. Furthermore, one of the previous problems of utilizing woodpulp fibers, or other cellulosic material, in an absorbent batt has been overcome. The tendency of the woodpulp fibers to collapse after contact with liquid, if any pressure is placed upon the absorbent core, has been eliminated by the presence of the first fibrous layer of resilient fibers which, in the presence of liquid, provide swelling space for the superabsorbent material and hence prevent collapse of the absorbent product. In other words, the layered structure actually becomes thicker in the presence of liquid as the superabsorbent swells and the resilient fibers yield to the swelling power of the superabsorbent and continue to provide void space or interstices for the continued swelling of the superabsorbent material. Once the liquid is absorbed the pressure placed upon the absorbent product, by normal use, does not release any liquid. The liquid remains permanently entrapped in the layered structure. Large amounts of liquid, over a reasonable period of time, are absorbed and are not released by pressure placed upon the layered structure by sitting on the absorbent product. Reasonably large amounts of exudate are received readily in the product in the apertures provided. The apertures receive liquid quickly and because of high exposure of superabsorbent material and wicking material the liquid is quickly absorbed into the layered structure. Furthermore, the liquid is continuously and rapidly transported to heretofore unused portions of the layered structure. The apertures tend to readily accept and store liquid in an available form for the adjacent superabsorbent material to gradually absorb the liquid and hence, make efficient use of the superabsorbent material present. The overall result is a drier product.

From the foregoing, it would be observed that numerous variations and modifications may be effected without departing from the true spirit and scope of the novel concept of this invention.

What is claimed:

1. An absorbent product comprising a layered structure, which structure is comprised of a first fibrous layer substantially of resilient fibers and containing at least about 10% by weight superabsorbent and a second layer of hydrophilic porous material, said layers being substantially coextensive superposed one on the other and subjected to at least about 200 psi pressure in the presence of from about 10% to about 50% moisture to form said structure, said structure being provided with longitudinally parallel slits in staggered rows, said slits being at least about 0.5 inch in length, said rows being from about 0.1 to about 0.5 inches apart, said slit structure being extended transversely to provide an apertured structure, and said apertured layered structure being sandwiched between a liquid-impermeable barrier and a liquid-permeable facing.

2. An absorbent product in accordance with claim 1 wherein said first fibrous layer is substantially of fibers which are both wet and dry resilient.

3. An absorbent structure in accordance with claim 2 wherein said fibrous web is a nonwoven web.

4. An absorbent product in accordance with claim 3 wherein said nonwoven web is a polyester web comprising a minor portion of binder fibers.

5. An absorbent product in acordance with claim 3 wherein said nonwove web is comprised of bicomponent fibers.

6. An absorbent product in accordance with claim 1 wherein said hydrophilic porous material is selected from the group consisting of open-cell cellulosic foam, cellulosic fibers, peat moss, acrylic fibers and mixtures thereof.

7. An absorbent product in accordance with claim 6 wherein said cellulosic fibers are woodpulp fibers, cotton linters, rayon fibers or mixtures thereof.

8. An absorbent product in accordance with claim 1 wherein said superabsorbent is present in an amount from about 20% to about 90% of the weight of said first fibrous layer.

9. An absorbent product in accordance with claim 1 wherein said product is a disposable diaper.

10. An absorbent product in accordance with claim 1 wherein said product is a sanitary napkin.

11. An absorbent product in accordance with claim 1 wherein said product is a wound dressing.

* * * * *

UNITED STATES PATENT AND TRADEMARK OFFICE
CERTIFICATE OF CORRECTION

PATENT NO. : 4,560,372

DATED : December 24, 1985

INVENTOR(S) : Heinz A. Pieniak

It is certified that error appears in the above-identified patent and that said Letters Patent is hereby corrected as shown below:

Claim 5 line 31: "nonwove" should read --nonwoven--.

Signed and Sealed this

Fifteenth Day of July 1986

[SEAL]

Attest:

DONALD J. QUIGG

Attesting Officer

Commissioner of Patents and Trademarks